United States Patent [19]
Keimel et al.

[11] Patent Number: 5,117,824
[45] Date of Patent: Jun. 2, 1992

[54] APPARATUS FOR MONITORING ELECTRICAL PHYSIOLOGIC SIGNALS

[75] Inventors: John G. Keimel, New Brighton; Joseph A. Ballis, Shoreview; Glenn M. Roline, Anoka, all of Minn.

[73] Assignee: Medtronic, Inc., Minneapolis, Minn.

[21] Appl. No.: 612,760

[22] Filed: Nov. 14, 1990

[51] Int. Cl.⁵ .............................................. A61N 1/39
[52] U.S. Cl. .......................... 128/419 D; 128/419 PG
[58] Field of Search ..................... 128/419 PG, 419 D

[56] References Cited

U.S. PATENT DOCUMENTS

| | | | |
|---|---|---|---|
| 4,819,643 | 4/1989 | Menken | 128/419 D |
| 4,974,589 | 12/1990 | Sholder | 128/419 PG |
| 5,048,521 | 9/1991 | Pless et al. | 128/419 PG |

OTHER PUBLICATIONS

"Reliable R-Wave Detection from Ambulatory Subjects" by Nitish V. Thakor, Biomed Sci Instrum 14:67-72, 1978.
"Design of Microcomputer-Based Medical Instrumetation" by W. J. Tompkins & John G. Webster, Editors Prentice-Hall, 1981 pp. 413-415.

Primary Examiner—William E. Kamm
Assistant Examiner—Scott M. Getzow
Attorney, Agent, or Firm—Reed A. Duthler; Harold R. Patton

[57] ABSTRACT

An implantable cardiac pacemaker and/or cardioverter/defibrillator employing an R-wave detector which atuomatically adjusts its sensing threshold in response to R-wave amplitude. The R-wave detector produces an output which is used to indicate the occurrence of ventricular contractions, and is used to reset the timing of the pacemaker and to indicate the occurrence of ventricular contractions for purposes of activating the associated cardioverter/defibrillator. Adjustment of the threshold is disable for a predetermined period following the delivery of each pacing pulse such that in the presence of continuous pacing for a predetermined period of time, the sensing threshold is returned to a desired, lower threshold level, allowing for detection of lower level R-waves, which may be indicative of tachyarrhythmia or fibrillation. The R-wave detector disclosed also eliminates the necessity for blanking of the input of the sense amplifier following sensing of naturally occurring R-waves, without increasing susceptibility to sensing of spontaneous T-waves which occur thereafter.

13 Claims, 3 Drawing Sheets

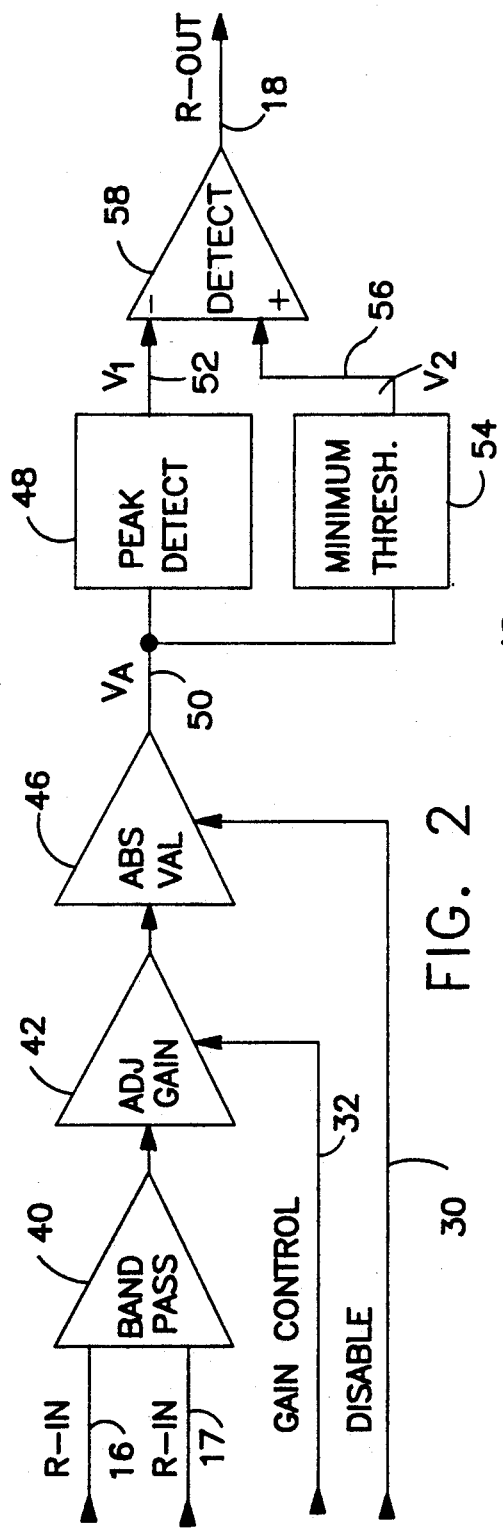
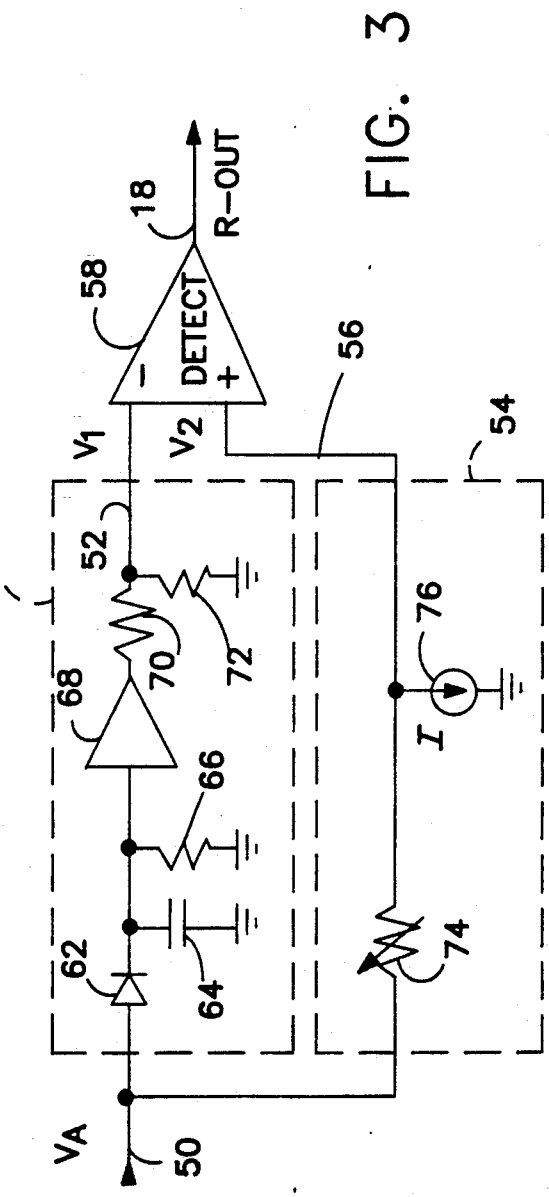

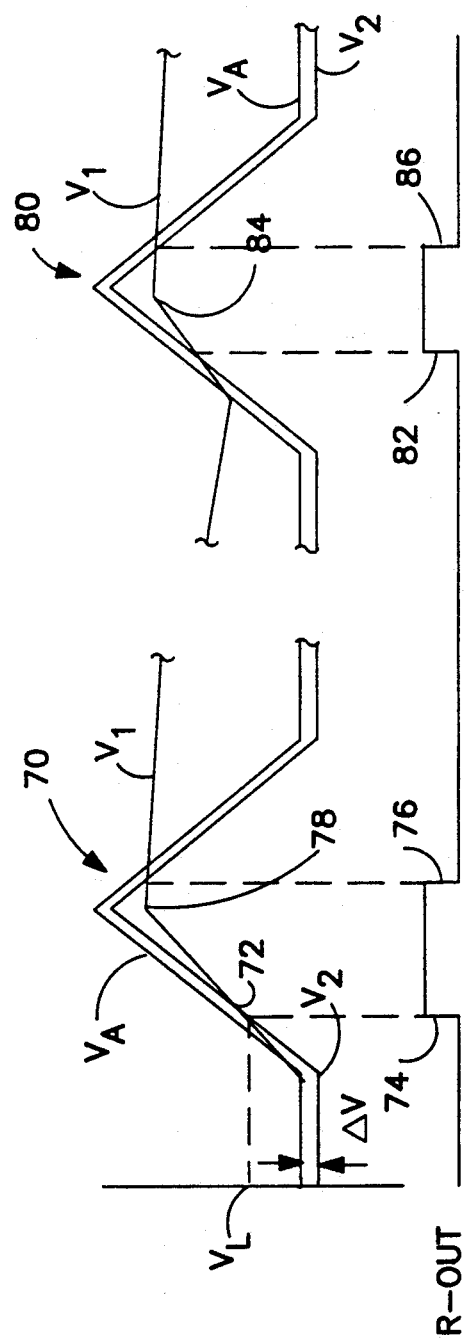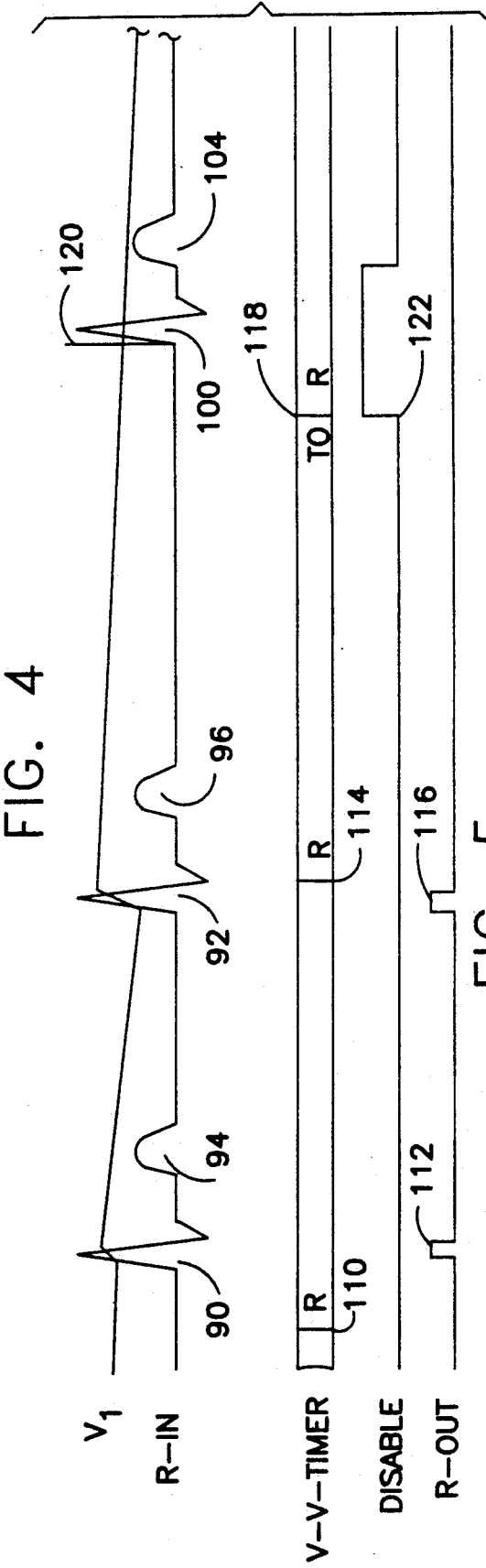

APPARATUS FOR MONITORING ELECTRICAL PHYSIOLOGIC SIGNALS

BACKGROUND OF THE INVENTION

The present invention relates generally to implantable medical devices and more particularly to implantable pacemakers and to implantable pacemakers associated with implantable cardioverters and/or defibrillators.

Traditionally, implantable cardiac pacemakers have employed R-wave detector circuitry which includes an R-wave amplifier in series with a detector circuit which detects the excursion of the amplified R-wave signal past a predetermined threshold. Adjustment of the sensitivity of the R-wave detection circuitry has been accomplished both by adjusting the gain of the R-wave amplifier and by adjusting the threshold of the detector. Normally, these adjustments are accomplished during programming of the implanted pacemaker, and the selected gain and/or threshold remains constant until reprogramming at a later date.

In the field of physiologic monitoring generally, it has been known for some time that it is desirable to employ an R-wave detector in which the detection threshold is varied in response to the amplitude of the detected R-waves. Circuitry for accomplishing this is disclosed in the book, *Design of Microcomputer-Based Medical Instrumentation* by W. J. Tompkins and John G. Webster, Editors, Prentice-Hall, 1981, pages 413 through 415, as well as in the article, "Reliable R-wave Detection from Ambulatory Subjects" by Thakor, et al., published in *Biomedical Science Instrumentation*, Volume 14, pages 67 through 72, 1978, both of which are incorporated by reference in their entireties. In these disclosed R-wave detectors, the half-wave rectified output of the R-wave amplifier is provided to a sample and hold circuit which provides an adjustable threshold proportional to the amplitude of the R-wave. This threshold gradually declines with time, returning to a base threshold level after a period of approximately ten seconds or so.

Sense amplifiers having automatic gain control are also known in the specific context of implantable pacemakers associated with cardioverters and defibrillators. U.S. Pat. No. 4,819,643 issued to Menken discloses an automatic gain control amplifier in which gain is gradually increased following sensed ventricular contractions, including both spontaneous ventricular contractions and paced ventricular contractions. This amplifier is used to provide a heart rate signal to a microprocessor, for purposes of activating an implanted defibrillator. The device also includes a cardiac pacemaker, which includes a sense amplifier as discussed above, having a gain level adjustable by means of programming. The cardiac pacemaker is provided with a hysteresis feature wherein a substantially longer interval (two seconds or greater) following a sensed ventricular contraction is provided prior to delivery of a cardiac pacing pulse, to allow the gain of the AGC sense amplifier to maximize prior to pacing.

SUMMARY OF THE PRESENT INVENTION

The present invention is particularly valuable in the context of a pacemaker/cardioverter/defibrillator. The R-wave detector is used to provide signals indicative of the occurrence of R-waves, both for resetting the pacemaker timing, and as an input to the tachycardia and fibrillation detection circuitry of the cardioverter and defibrillator. The present invention provides an automatically adjustable R-wave detection system which can be used in the context of a normally functioning VVI type pacemaker, while still retaining the ability to sense low level signals indicative of tachycardia or fibrillation for purposes of initiating tachyarrhythmia and/or defibrillation therapies. The present invention is also particularly valuable in the context of a pacemaker/cardioverter/defibrillator in which cardiac antitachy pacing therapies are delivered at rates substantially in excess of normal pacing rates.

The detection circuit defines a detection threshold which is defined as a predetermined proportion of the amplitude of a detected R-wave, and which decays over a period of about three seconds or less thereafter to a fixed, lower threshold level. Preferably, the detection threshold should decay to its minimum value in about one second or less. Redefinition of the threshold level is prevented for a predetermined period following delivery of a pacing pulse, so that during cardiac pacing, the threshold of the detector will return to its lowest level. This allows for detection of low level spontaneous R-waves which may be indicative of tachycardia or fibrillation, during pacing. Because the output of the detector is coupled to both the pacemaker circuitry and to the defibrillation and cardioversion detection circuitry, the detected low level R-waves will be effective to inhibit the pacemaker and for use in detection of fibrillation or tachycardias.

This functional interrelation of the R-wave detector with the pacing and cardioversion circuitry is believed to have substantial advantages over the configuration illustrated in the above-cited Menken patent, in which sensing of low-level R-waves is dependent on the absence of cardiac pacing, requiring the employment of a hysteresis-type pacemaker with a prolonged escape interval following a sensed ventricular contraction prior to delivery of a cardiac pacing pulse. The specific embodiment of the present invention disclosed below also has the advantage that it eliminates the necessity of blanking the input to the R-wave detection circuitry following a sensed R-wave, which otherwise would be necessary if sensing of low level R-waves is desired without T-wave sensing. The invention thus simplifies the construction and the operation of the device and allows for sensing of rapid R-waves and low level R-waves such as those associated with fibrillation without sensing T-waves.

BRIEF DESCRIPTION OF THE DRAWINGS

FIG. 2 is a block, functional diagram of the R-wave detector circuitry of the present invention, and its functional interconnections with the cardiac pacemaker portion of the pacemaker/cardioverter/defibrillator illustrated in FIG. 1.

FIG. 3 is a more detailed, functional schematic illustrating the operation of the peak detector and threshold adjustment portion of the circuitry illustrated in FIG. 2.

FIG. 4 is a timing diagram illustrating the values of signals taken from various points in the circuitry illustrated in FIGS. 2 and 3.

FIG. 5 is a timing diagram illustrating the functioning of the R-wave detector circuitry in conjunction with the pacing circuitry illustrated in FIG. 1.

DETAILED DESCRIPTION OF THE INVENTION

Figure 1:
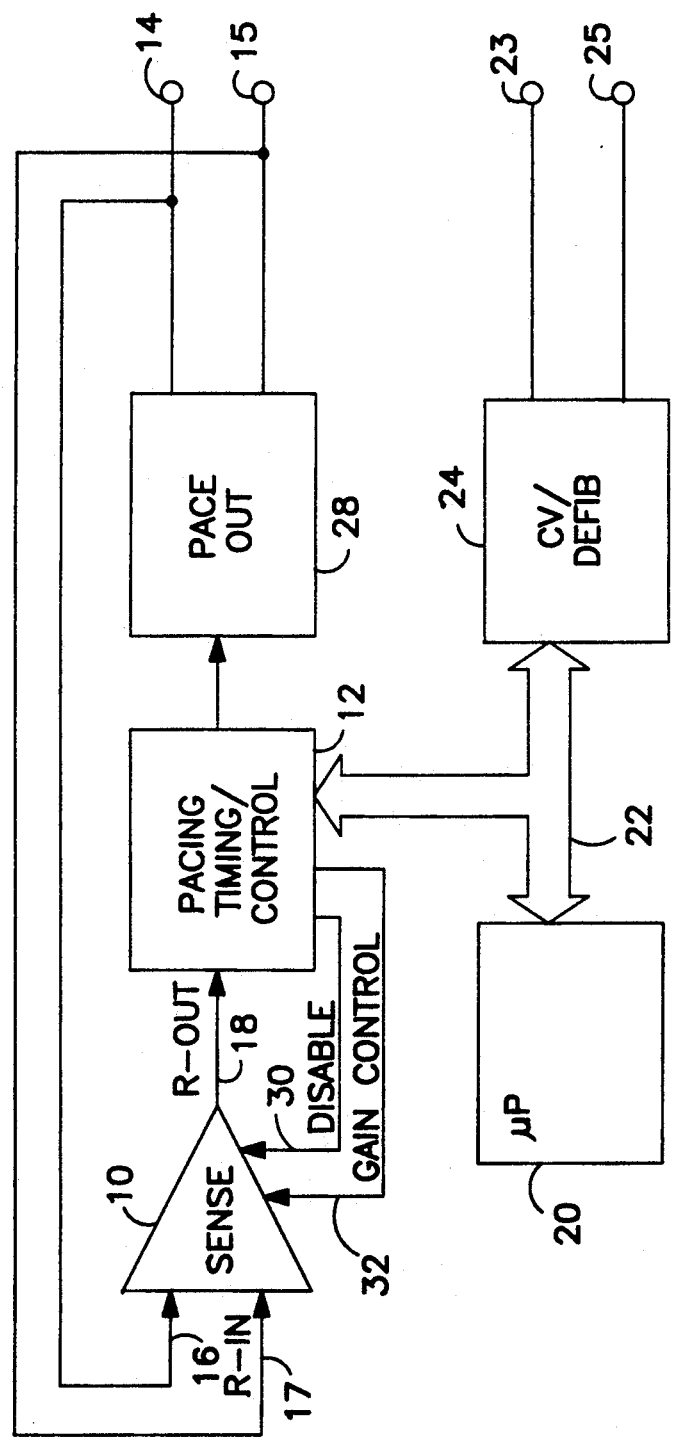
FIG. 1 is a block, functional diagram of the interrelation of the R-wave detection circuitry with a pacemaker/cardioverter/defibrillator.

FIG. 1 is a block, functional diagram illustrating the functional interrelation of the R-wave detection circuitry of the present invention in conjunction with a pacemaker/cardioverter/defibrillator. The R-wave detector 10 interfaces primarily with the cardiac pacemaker timing circuitry 12. As illustrated, the R-wave detector 10 is coupled to the heart by means of electrodes 14, 15. Electrical signals from electrodes 14 and 15 are provided to the R-wave detector 10 by means of R-IN lines 16 and 17. In response to detection of an R-wave, R-wave detector 10 provides a digital logic signal on R-OUT line 18, which serves to reset the basic pacing interval (V—V interval) of the pacing circuitry 12. This occurrence of this logic signal is also communicated to a microprocessor 20 by means of logic signals on control/data bus 22. Microprocessor 20 also controls the functions of the pacing circuitry 12 and the operation of cardioverter/defibrillator 24 by means of control/data bus 22. Pacer circuitry 12 includes a plurality of timers which operate under the control of microprocessor 20 to define blanking, refractory and V—V intervals and pulse widths for both VVI bradycardia pacing and antitachycardia pacing. Cardioverter/defibrillator 24 provides high energy defibrillation and cardioversion pulses to the heart by means of large surface area electrodes 23, 25, which may be any such electrodes known to the art.

The present invention is believed practicable in the context of any implantable pacemaker/cardioverter/defibrillator, including devices as disclosed in U.S. Pat. No. 4,548,209, issued to Wielders, et al, U.S Pat. No. 4,693,253, issued to Adams, U.S. Pat. No. 4,375,817, issued to Engle, et al, U.S. Pat. No. 4,384,585, issued to Zipes or U.S. Pat. No. 4,830,006, issued to Haluska, et al, all of which are incorporated herein by reference in their entireties.

If the pacing circuitry 12 does not receive a signal on R-OUT line 18 for a predetermined period of time, corresponding to the escape interval of the cardiac pacemaker (V—V interval), the pacing circuitry 12 will trigger generation of a cardiac pacing pulse by ventricular output stage 28. Prior to and following delivery of a ventricular pacing pulse by output stage 28, the pacing circuitry generates a disable signal on line 30, which prevents adjustment of the sensing threshold by R-wave detector 10. Gain control line 32 from pacing circuitry 12 adjusts the overall gain of the amplifier circuitry within detector 10.

FIG. 2 shows a more detailed functional diagram of the R-wave detection circuit 10. Electrical signals on R-IN lines 16 and 17 are filtered by band pass filter 40, and passed through an adjustable gain circuit 42, with the degree of amplification controlled by logic signals on gain control line 32. In most embodiments, it is anticipated that this gain adjustment will be accomplished by a means of telemetry from a programmer external to the body, much along the lines of prior art adjustable gain amplifiers as employed in implantable devices. The amplified R-wave signal is thereafter passed through an absolute value circuit 46, which produces a rectified output signal $V_A$ on line 50, reflecting the absolute value of the filtered and amplified input signal. Absolute value circuit 46 is disabled via disable line 30 for a predetermined period preceding and following the delivery of each cardiac pacing pulse or high energy cardioversion or defibrillation pulse.

The output of absolute value circuit 46 is passed through a peak detect circuit 48 which provides an output voltage $V_1$ on line 52, which is a fraction of $V_A$ and rises rapidly with the voltage $V_A$ on line 50, and which decays slowly thereafter. The voltage $V_A$ on line 50 is also passed through minimum threshold circuitry 54, which produces an output voltage $V_2$ on line 56, equal to the voltage $V_A$, minus a predetermined voltage differential $\Delta V$. Comparator 58, which serves as the detection portion of the circuit, generates a high logic signal on R-OUT line 18 in response to $V_2$ on line 56 exceeding $V_1$ on line 52. The operation of the peak detector, minimum threshold, and comparator circuitry is discussed in more detail in conjunction with FIGS. 2 and 3 below.

FIG. 3 is more detailed functional diagram of the peak detect circuitry 48 and minimum threshold circuitry 54. The components illustrated are intended to model the desired behavior of the circuit, and to indicate the general type of peak detection functions that are desired. The specific implementation of the circuitry can vary substantially, and still remain within the scope of the invention. However, the functional aspects described are believed to reflect the best mode of practicing the invention, known to the inventors.

The peak detector 48 is modeled as consisting of an ideal diode 62 (a functional circuit which prevents reverse current through, without substantial voltage drop in the forward direction, typically taking the form of a transistor network), a capacitor 64, a bleed off resistor 66, a buffer amplifier 68, and a voltage divider network comprising resistors 70 and 72. Capacitor 64 is chosen so that it can follow the voltage $V_A$ on line 50, within the current output constraints of the absolute value circuit 46. Bleed off resistor 66 allows discharge of capacitor 64. The voltage on capacitor 64 is buffered by amplifier 68, and divided by resistors 70 and 72 to provide a voltage $V_1$ on line 52 equal to approximately three-quarters of the voltage on capacitor 64. This value $V_1$ serves as the variable detection threshold.

The absolute value circuit 46 is conventionally designed such that its output will be limited to a predetermined maximum voltage. The values of capacitor 64 and resistor 66 are preferably chosen such that capacitor 64 will bleed off to its minimum voltage level over a period of about two seconds or less. A time constant of about 0.6 seconds is believed appropriate. The minimum threshold circuitry 54 is modeled as including an adjustable resistor 74 and a current sink 76. As a result, the voltage $V_2$ on line 56 is equal to the voltage $V_A$ on line 50, minus a voltage differential $\Delta V$ defined by adjustable resistor 74 and the current I through current sink 76. The value of adjustable resistor 74 determines the effective lowest threshold level for the detector circuit, as illustrated in FIG. 4, and is used to adjust for small differences in gain and offset voltage in the various circuitry components.

FIG. 4 is a timing diagram illustrating the circuit modeled in FIG. 3. The timing diagram begins at a state in which the capacitor 64 is fully discharged, so that the voltage $V_A$ and the voltage $V_1$ are equal. The voltage $V_2$ is less than the voltage $V_A$ by $\Delta V$. With the occurrence of the first R-wave, generally illustrated at 70, voltage $V_A$ rises rapidly, along with voltage $V_2$. Capacitor 64 is charged up to a voltage equal to $V_A$, so that voltage $V_1$ is approximately three-quarters of voltage $V_A$, during the rising portion of the detected R-wave 70. Because the voltage $V_1$ does not rise as rapidly as voltage $V_A$, at a point 72, voltage $V_1$ and voltage $V_2$ are equal, triggering detector 58 to generate a positive logic signal 74 on R-OUT line 18. The voltage $V_L$ at which the voltages $V_1$ and $V_2$ are equal defines the effective lower threshold $V_L$, as illustrated. Adjustment of the variable resistor 74 allows for adjustment of the value of $\Delta V$, and thus the adjustment of the value of minimum threshold $V_L$. After the peak of the R-wave 70, capacitor 64 begins to slowly discharge, resulting in the gradual decrease in the value of voltage $V_1$. At the point 78 that voltage $V_1$ and voltage $V_2$ are again equal, the digital logic signal on R-OUT line 18 returns to a low logic level at 76.

In between detected R-waves, capacitor 64 continues to gradually discharge. A second R-wave, generally illustrated at 80 occurs, with corresponding increases in $V_A$, $V_1$ and $V_2$. Because capacitor 64 still retains a substantial amount of charge from the previous R-wave 70, it does not begin to charge up until after the voltage $V_A$ is greater than the voltage already stored on capacitor 64. At the point at which the value of voltage $V_2$ is greater than $V_1$, the detector 58 provides a high logic level signal at 82, on V-OUT line 18. As $V_A$ increases beyond the voltage stored on capacitor 64, the capacitor begins to charge, following the increase in voltage $V_A$, as illustrated at 84, until the peak of the R-wave 80. As discussed in conjunction with the previous R-wave 70, the R-OUT line 18 from detector 58 is set low at 86 when $V_2$ falls below the value of $V_1$.

In use, The R-wave detector as disclosed provides several important benefits. First, because the sensing threshold is adjusted with each sensed R-wave, sensing of the lower amplitude T-waves which follow is avoided. However, the rapid decay (e.g. two seconds or less) of the adjusted threshold allows for a rapid return to a low threshold appropriate for sensing high rate tachycardia beats or fibrillation. The rapid decay also allows for the sense amplifier to track rapid variations in the amplitude of R-waves associated with tachycardia or fibrillation. Because the threshold is not adjusted in response to a paced R-wave, sensing of tachycardias or fibrillation during pacing is improved.

In this context, it should be kept in mind that the amplitude of paced R-waves may be substantially higher than the amplitude of spontaneous R-waves. As a result, thresholds adjusted on the basis of paced R-waves may be too high to allow for detection of some high rate tachycardias or fibrillation. Moreover, during anti-tachycardia pacing, intervals between pacing pulses may be too short to allow sensing thresholds to decay substantially between paced R-waves. In a device embodying the present invention, however, the sensing threshold will decay to and remain at its minimum level throughout anti-tachycardia cardiac pacing, allowing for effective sensing even during high rate pacing.

As discussed above, the functional characteristics of peak detection circuitry illustrated are believed to provide the best mode of practicing the invention, known to the inventors. However, it is believed the invention could also be practiced employing an auto-thresholding R-wave detector as illustrated in the above-cited Tompkins et al. and Thakor et al. articles. In these disclosed R-wave detectors, however, the value of the threshold set by the peak detector can apparently quickly decrease by a significant amount as a result of a decrease in amplitude of detected R-waves. This is believed to provide a workable auto-thresholding R-wave detector. However, the time constant disclosed therein of ten seconds, which would be in effect in the case in which detectable R-waves abruptly ceased is believed to be too long for use in conjunction with an implantable pacemaker/cardioverter/defibrillator, where it is desirable to be able to resume detection of low level R-waves as soon as possible after cessation of high amplitude R-waves. Nonetheless, it is believed that a circuit as disclosed in these articles, or other similar circuits may usefully be used or adapted for use in the context of the present invention.

FIG. 5 is a timing diagram illustrating the overall interrelation of the auto-thresholding R-wave detector with the cardiac pacing circuitry illustrated in FIG. 1. A simulated EKG strip is illustrated as the input to R-IN lines 16, 17 (FIG. 1). The EKG illustrated includes two spontaneous R-waves 90 and 92 followed by T-waves 94 and 96, respectively. The EKG strip also illustrates a paced R-wave 100 followed by T-wave 104. The operation of the pacemaker circuitry is illustrated by means of a timing chart illustrating the operation of the internal, escape interval timer therein. As is typical VVI type pacemakers, this timer (the V—V timer) is reset on either its own time out or on sensing of a spontaneous R-wave. At time out of the V—V timer, a ventricular pacing pulse is triggered. In the timing strip illustrating the operation of the pacemaker circuitry, "R" indicates reset of the V—V timer and "TO" indicates time out. Also illustrated are the logic signals on disable line 30 (FIG. 1) and R-OUT line 18.

The initial R-wave 90, because it has an amplitude greater than the threshold then in effect as reflected by the value of $V_1$, results in the generation of a digital logic signal 112, on R-OUT line 18 and resets the V—V timer at 110. As illustrated, it also results in an adjustment of the detection threshold as reflected by an increase of the value of $V_1$. The value of $V_1$ is sufficiently high to prevent sensing of the next subsequent T-wave 94.

Because the next subsequent R-wave 92 occurs prior to time out of the V—V timer, the V—V timer is again reset at 114, a digital logic signal 116 is generated on R-OUT line 18, and the threshold is again adjusted as indicated by an increase in the value of $V_1$.

Because no spontaneous R-waves are detected prior to time out of the V—V interval timer at 118, the pacing circuitry 12 triggers a pacing pulse 120, triggering paced R-wave 100. In response to the delivery of pacing pulse 120, disable line 30 (FIG. 1) is set high for a predetermined period at 122, preventing R-wave 100 from resetting the sensing threshold. This is indicated by the continued low level of $V_1$. The sensing threshold has returned to its lowest effective level, allowing for detection of low level R-waves following ventricular pacing.

Although the device disclosed above takes the form of a cardioverter for treating ventricular tachyarrhythmias, the invention may also be usefully practiced in devices intended to sense and treat atrial arrhythmias. Moreover, the adjustable threshold detector may also be usefully employed in pacemakers which sense electrical signals in either the ventricle (R-waves) or atrium, (P-waves) even in the absence of an associated cardioverter. While such devices may not be able to initiate tachyarrhythmia treatments, the ability to sense the presence of tachyarrhythmias may still be useful for diagnostic purposes, and for determining the appropriateness of anti-bradycardia pacing therapies. As such, the embodiment disclosed above should be considered exemplary, rather than limiting with regard to the claims that follow.

In conjunction with the claims below, the term "cardioverter" is used generically. That is, it is intended to include devices which deliver any known form of therapy for terminating tachyarrhythmias. Such therapies would include, without limitation, anti-tachyarrhythmia pacing therapies employing pulses of an amplitude similar to cardiac pacing pulses, and high energy single and multiple pulse cardioversion and defibrillation therapies and triggered drug delivery systems.

In conjunction with the above disclosure, we claim:

1. In an implantable cardioverter comprising means for detecting a tachyarrhythmia and means for treating said tachyarrhythmia, said cardioverter also comprising pulse generator means for generating cardiac pacing pulses, the improvement comprising:

variable threshold R-wave detector means for detecting the occurrence of R-waves and for providing output signals indicative of the detection of said R-waves, said signals provided to said tachyarrhythmia detection means, said variable threshold R-wave detector means comprising means for defining an R-wave detection threshold and means for adjusting said R-wave detection threshold to a value based upon the amplitude of a detected R-wave and further includes means for gradually reducing said R-wave detection threshold following said detected R-wave;

cardiac pacemaker timing means for defining a V—V interval and for triggering said pulse generator means at the expiration of said V—V interval, said timing means reset by the output of said R-wave detector means; and disable means for disabling said threshold adjusting means from adjusting said R-wave detection threshold in response to an R-wave following a cardiac pacing pulse from said pulse generator means.

2. An implantable cardioverter according to claim 1, wherein said R-wave detector means further comprises means for defining a minimum R-wave detection threshold.

3. An implantable cardioverter according to claim 1 or claim 2 wherein said threshold adjusting means comprises means for adjusting said R-wave detection threshold to be equal to a predetermined proportion of the amplitude of said detected R-wave.

4. An implantable cardioverter according to claim 3 wherein said predetermined proportion of the amplitude of said detected R-wave is approximately 75% of said detected R-wave.

5. An implantable cardioverter according to claim 1 wherein said R-wave detector means comprises means for allowing said R-wave detection threshold to decrease to said minimum R-wave detection threshold over a predetermined period of three seconds or less.

6. In a device comprising pulse generator means for generating cardiac pacing pulses for delivery to a chamber of the heart, the improvement comprising:

variable threshold detector means for detecting the occurrence of electrical heart signals from said chamber of the heart and for providing output signals indicative of the detection of said electrical heart signals, said variable threshold detector means comprising means for defining a detection threshold and means for adjusting said detection threshold to a value based upon the amplitude of a detected electrical heart signal, and further includes means for gradually reducing said detection threshold following said detected electrical heart signal;

cardiac pacemaker timing means for defining a V—V interval and for triggering said pulse generator means at the expiration of said V—V interval, said timing means reset by said output signal from said detector means; and disable means for disabling said threshold adjusting means from adjusting said detection threshold in response to a said electrical heart signal following a cardiac pacing pulse from said pulse generator means.

7. A device according to claim 6, wherein said detector means further comprises means for defining a minimum detection threshold.

8. A device according to claim 6 or claim 7 wherein said threshold adjusting means comprises means for adjusting said detection threshold to be equal to a predetermined proportion of the amplitude of said detected electrical heart signal.

9. A device according to claim 8 wherein said predetermined proportion of said amplitude of said detected electrical heart signal is approximately 75% the amplitude of said detected electrical heart signal.

10. A device according to claim 6 wherein said detector means comprises means for allowing said detection threshold to decrease to said minimum detection threshold over a predetermined period of three seconds or less.

11. A device according to claim 10 wherein said predetermined period is one second or less.

12. A device according to claim 6 wherein said chamber of the heart is the ventricle.

13. A device according to claim 6 wherein said device further comprises a cardioverter including means for detection of tachyarrhythmias responsive to said output signals from said detector means and means for treating tachyarrhythmias so detected.

* * * * *